United States Patent
Meier et al.

(10) Patent No.: US 6,723,814 B2
(45) Date of Patent: Apr. 20, 2004

(54) AMPHIPHILIC COPOLYMER PLANAR MEMBRANES

(75) Inventors: Wolfgang Meier, Basel (CH); Corinne Nardin, St. Louis (FR); Mathias Winterhalter, Toulouse (FR)

(73) Assignee: BioCure, Inc., Norcross, GA (US)

( * ) Notice: Subject to any disclaimer, the term of this patent is extended or adjusted under 35 U.S.C. 154(b) by 0 days.

(21) Appl. No.: 09/859,177

(22) Filed: May 16, 2001

(65) Prior Publication Data

US 2002/0037986 A1 Mar. 28, 2002

Related U.S. Application Data

(60) Provisional application No. 60/204,456, filed on May 16, 2000.

(51) Int. Cl.[7] .............................. C08F 2/46; C08F 30/08
(52) U.S. Cl. .................... 526/279; 526/303.1; 526/297; 526/291; 526/317.1; 526/310; 526/308; 526/307.4; 526/318; 526/318.25; 526/318.41; 526/332; 526/335; 526/346; 526/348; 522/60; 522/31; 522/84; 522/86; 522/87; 522/91; 522/96; 522/148; 522/172; 522/150; 522/151; 522/152; 522/153; 522/154; 522/157; 522/173; 522/178; 522/181; 522/182
(58) Field of Search .............................. 526/279, 303.1, 526/297, 291, 317.1, 310, 308, 307.4, 318, 318.25, 318.41, 332, 335, 346, 348; 522/84, 86, 87, 91, 96, 99, 148, 172, 150, 151, 152, 153, 154, 157, 173, 178, 181, 182

(56) References Cited

U.S. PATENT DOCUMENTS

| | | | |
|---|---|---|---|
| 3,929,509 A | | 12/1975 | Taskier |
| 4,661,442 A | | 4/1987 | Lukens |
| 4,942,204 A | * | 7/1990 | Kennedy ..................... 525/279 |
| 5,073,381 A | * | 12/1991 | Ivan et al. ................... 424/487 |
| 5,080,936 A | | 1/1992 | Cerwen |
| 5,256,749 A | * | 10/1993 | Hickel et al. ............... 526/279 |
| 5,391,634 A | * | 2/1995 | Ladika et al. ............. 525/327.3 |
| 5,410,016 A | * | 4/1995 | Hubbell et al. ............. 128/898 |
| 5,435,919 A | * | 7/1995 | Ladika et al. ............... 210/638 |
| 5,567,435 A | * | 10/1996 | Hubbell et al. ............. 128/898 |
| 5,626,863 A | * | 5/1997 | Hubbell et al. ............. 128/898 |
| 5,679,482 A | | 10/1997 | Ehrenberg et al. |
| 5,702,717 A | * | 12/1997 | Cha et al. ................... 424/424 |
| 5,807,944 A | * | 9/1998 | Hirt et al. ................ 351/160 R |
| 5,874,316 A | | 2/1999 | Cornell et al. |
| 5,922,594 A | | 7/1999 | Lofs |
| 5,955,343 A | | 9/1999 | Holmes et al. |
| 6,004,573 A | * | 12/1999 | Rathi et al. ................. 424/426 |
| 6,060,582 A | * | 5/2000 | Hubbell et al. ............. 525/408 |
| 6,117,949 A | * | 9/2000 | Rathi et al. ................. 424/425 |
| 6,200,589 B1 | * | 3/2001 | Kennedy et al. ............ 424/424 |
| 6,201,072 B1 | * | 3/2001 | Rathi et al. ................. 424/425 |
| 6,306,922 B1 | * | 10/2001 | Hubbell et al. ............. 128/898 |
| 6,365,171 B1 | * | 4/2002 | Kennedy et al. ............ 424/422 |

FOREIGN PATENT DOCUMENTS

| | | | |
|---|---|---|---|
| JP | 101 10019 | 8/1996 | |
| WO | WO 9912059 A1 * | 3/1999 | ............ G02B/1/04 |
| WO | WO 00/26157 | 5/2000 | |

OTHER PUBLICATIONS

Benz. R., *J. of Bacteriol.* 162(12), 722 (1985).
Dutzler. R. et al., *Structure* 4(2), 127 (1996).
Eisenberg. B., *Acc. Chem. Res.* 31,117 (1998).
Kabanov, A.V. et al., *J. Controlled Release*, 22(2), 141–157 (Oct. 1, 1992).
Lakey, J. H., *FEBS Letters* 278(1):31–34 (1991).
Maassen, H.-P. et al., *Makromol. Chem., Macromol. Symp.* 39, 215 (1990).
Meier, W., *Macromolecules*, 31, 2212 (1998).
Meier, W. et al., Phys. Chem. Chem. Phys., 2(20):4559–4562 (2000).
Meier, W. et al., Angew Chem Int Ed Engl. 39(24):4599–4602 (2000).
Mueller, P. et al., *J. Phys. Chem.* 67, 534 (1963).
Nardin, C. et al., Langmuir. 16(20): 7708–7712 (Oct 2000).
Nardin, C. et al., Chimie 55: 142–146 (2001).
Njus, D., Fundamental Principles of Membrane Biophysics, Ch. 3 (2000).
Ringsdorf, et al., *Angew. Chem.*, 100, 117 (1988).
Salafsy, J. T., Biochemistry, 35:14773–14781 (1996).
Schellenberg et al., *Langmuir* 15, 1283 (1999).
Winterhalter, M., *Colloids and Surfaces A* 149, 547 (1999).
Yang, et al., *Colloid Polym. Sci.,* 270, 1080 (1992.
Yang, et al., *Macromolecules,* 25, 1786 (1992).
Yang, et al., *Macromolecules,* 25, 1791 (1992).
Zhang, et al., *Science,* 268, 1728 (1995).

* cited by examiner

*Primary Examiner*—James J. Seidleck
*Assistant Examiner*—Sanza L McClendon
(74) *Attorney, Agent, or Firm*—Collen A. Beard

(57) ABSTRACT

Membranes made from amphiphilic copolymers are disclosed. The amphiphilic copolymers can be ABA copolymers, where one of A and B is hydrophilic and the other is hydrophobic. The copolymers may be crosslinked to form more stable structures. Crosslinking can be accomplished using a variety of methods, including end to end polymerization of copolymers having terminal unsaturated groups. Molecules such as membrane proteins can be incorporated into the membrane to allow the transport there through of selected components.

16 Claims, 5 Drawing Sheets

US 6,723,814 B2

AMPHIPHILIC COPOLYMER PLANAR MEMBRANES

RELATED APPLICATION

This application claims priority to U.S. provisional application Serial No. 60/204,456, filed on May 16, 2000, entitled "Amphiphilic Copolymer Planar Membranes".

FIELD OF THE INVENTION

The present invention is generally in the field of planar membranes. More specifically, the invention is in the field of planar membranes made with self-assembling amphiphilic segmented copolymers.

BACKGROUND OF THE INVENTION

Self-organizing, or self-assembling, structures are known. A common example is liposomes. Liposomes are made by emulsifying amphiphilic (and optionally hydrophobic or lipophilic) molecules in water, preferably in the presence of surfactant. Liposomes are either unilamellar or multilamellar spheres that are manufactured from a variety of lipids. Drugs, for example, can be encapsulated within liposomes or captured within the liposome membrane. Other types of self-assembling structures include planar lipid membranes, which are termed Black Lipid Membranes in the art. Membranes are preferred over liposomes for applications where a flat surface is desired such as, for example, matrices for biological sensors.

Self-assembled structures known in the prior art have often exhibited limited stability. Cross-linked liposomes have been prepared which are more resistant to degradation. Liposomes having "pegylated" surfaces, i.e., surfaces having coated thereon or bonded thereto polyethylene glycol, have longer circulating times following administration to a patient. Other methods to prepare liposomes with enhanced stability include preparation techniques such as emulsion polymerization and interfacial polymerization. However, these techniques require rather aggressive reaction conditions, so sensitive substances cannot be used during these procedures. The stability of liposomes can be enhanced by surface grafting of hydrophilic polymers or by polymerization of reactive lipid molecules in the vesicular aggregates. Recently, a similar mechanical stabilization of vesicles was obtained by swelling the lipid bilayer of vesicles with hydrophobic monomers, which were subsequently polymerized.

Lipid bilayers are the basic constituent of biological membranes. The lipids serve as a fluid matrix for many membrane associated proteins responsible for various key functions such as signaling or transport. Many of these membrane proteins are pharmacologically important or have biotechnological potential. It would be advantageous to have an artificial membrane system in which they and other biological molecules can be immobilized. Such a system would provide a number of benefits, including the ability to use the immobilized protein in biosensors.

SUMMARY OF THE INVENTION

Membranes are made from segmented amphiphilic A+B copolymers, where A is hydrophilic and B is hydrophobic, which self-assemble when dispersed in water. In one embodiment, the membranes are freestanding, where the term "freestanding" refers to a membrane that is not supported on a substrate. In another embodiment, the membranes are supported on a substrate. In a preferred embodiment, the copolymer is a segmented copolymer, such as a triblock ABA copolymer. The segmented copolymer forms a membrane where the middle layer is hydrophobic, and the outer layers are hydrophilic. In another embodiment, the copolymer is a BAB copolymer. The membranes may be stabilized by end-group polymerization and/or by crosslinking of internal groups. The polymerization and crosslinking can be achieved via ionic bonds, covalent bonds, and/or through other types of bonds. In one embodiment, end groups of the copolymers are polymerized. Polymerization can achieved by any of a number of means, including photopolymerization, typically in the presence of a photoinitiator. Other types of polymerization are also possible, such as redox polymerization. In one embodiment, the membranes include proteins, such as membrane proteins, that allow the transport there through of selected components.

In general, planar membranes with a thickness ranging from about 1 to 100 nm, in one embodiment on the order of about 10 nm, can be prepared from a triblock amphiphilic copolymer. Stable films with areas from about 10 $nm^2$ to 10 $cm^2$, generally up to about 1 $mm^2$ can be made. The triblock copolymer can have polymerizable groups at both chain ends and/or at internal sites. These groups can be polymerized, by UV light, for example, after the formation of the self-assembled membrane. The mechanical properties of the membranes, as characterized by short electric fields, are significantly more cohesive than lipid bilayers, as seen by the higher critical voltages required for rupture. Polymerization further increases the stability of the membranes.

Molecules can be reconstituted in the block copolymer membranes. In one embodiment the molecule is a lipid membrane protein. The protein remains functional in the completely artificial surrounding even after polymerization of the membrane.

The materials disclosed herein could be used for a number of purposes, such as biosensors, non-linear optical devices, coatings, in diagnostics, for drug delivery, and for other applications.

DETAILED DESCRIPTION OF THE PREFERRED EMBODIMENTS

Definitions

Figure 1:
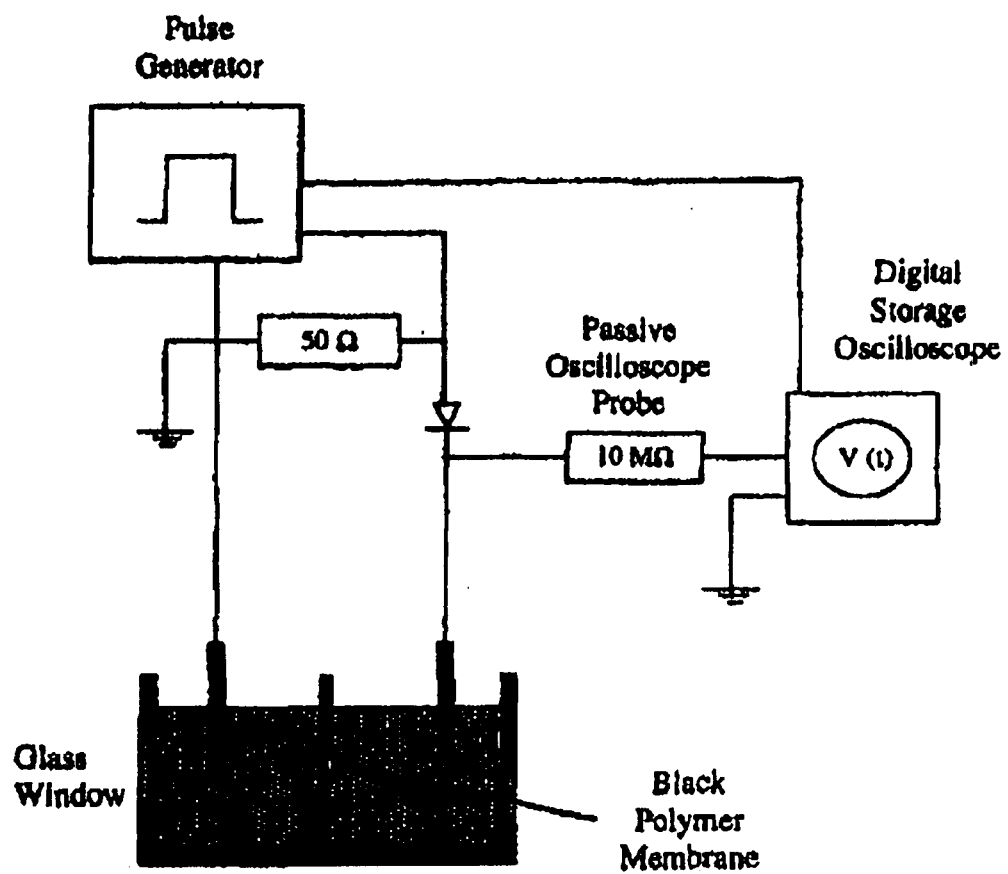
FIG. 1 is a schematic of charge pulse instrumentation used to induce and record irreversible rupture and to measure the conductance of copolymer membranes.

The term polymerization as used herein refers to end to end attachment of the amphiphilic copolymers.

The term crosslinking as used herein refers to interpolymer linking of all types, including end to end attachment as well as covalent or ionic bonding of any portion of a copolymer to another copolymer. Crosslinking can be through end groups or internal groups and can be via covalent, ionic, or other types of bonds.

Segmented copolymers, containing at least one hydrophilic A segment and at least one hydrophobic B segment, that self-assemble to form membranes, and methods for making such membranes, are disclosed. The copolymers are primarily described herein as block copolymers. It should be understood that this term refers to linear block copolymers as well as various other structures, such as graft and comb structures, containing both A and B segments.

The formation of membranes from the copolymers is a result of the amphiphilic nature of the segmented copolymers. The aggregation occurs via non-covalent interactions and therefore is reversible. The membranes can be polymerized and/or crosslinked to provide additional stability. It should be understood that the copolymers can be polymerized via end groups, crosslinked via internal crosslinkable groups, or a combination of end group and internal group polymerization/crosslinking can be used. If the membranes are polymerized using covalent bonds, the resulting membranes are more stable and may preserve their morphology even after they are removed from an aqueous solution.

The stability of a particular membrane depends in a large part on the strength of the hydrophobic and hydrophilic interactions between the copolymers. The strength also depends upon the stability of the junction between the hydrophilic and hydrophobic segments and the juncture between the hydrophilic or hydrophobic segment and the polymerizing unit, if one is used. The stability further depends upon the strength of the polymerization bond or crosslinking. The stability of the membrane can be decreased by the introduction of weak links, such as biodegradable links or ionic crosslinks, between the hydrophilic and hydrophobic segments, within the hydrophilic or hydrophobic segment, or between the hydrophilic or hydrophobic segment and the polymerizing unit.

Crosslinking can be achieved using many standard techniques, including photopolymerization, for example, of acrylate groups in the presence of a photoinitiator, or through the use of an alkylating agent. Crosslinking can be achieved using side groups and end groups which can be polymerized by free radical polymerization, side groups which can be polymerized by cationic polymerization, and side groups which can be polymerized by ring-opening polymerization.

In addition to the hydrophilic and hydrophobic segments, the membranes may also include additional hydrophobic and/or hydrophilic components, as well as crosslinkers such as monomers or macromers with reactive groups, surfactants, and crosslinking initiators, especially photoinitiators.

I. The Amphiphilic Copolymers

The membranes are made from segmented copolymers including alternating hydrophilic and hydrophobic segments. In a preferred embodiment, the copolymers are ABA copolymers, where A is the same or different hydrophilic segments and B is a hydrophobic segment.

One class of suitable amphiphilic polymeric materials is described in U.S. Pat. No. 5,807,944 to Hirt et al. Since the materials disclosed therein are primarily for use as contact lens, it is highly desirable that the materials be oxygen and ion permeable. That is not a requirement for other applications and in fact may not be desirable in some applications. In a preferred embodiment, the amphiphilic polymer is biocompatible. Many suitable amphiphilic copolymers and hydrophilic and hydrophobic polymers are taught in WO 97/49387.

A. Hydrophilic and Hydrophobic Segments

The amphiphilic segmented copolymer includes at least one segment B that includes a hydrophobic polymer. Any of a number of hydrophobic polymers can be used, such as, but not limited to, polysiloxane such as polydimethylsiloxane and polydiphenylsiloxane, perfluoropolyether, polystyrene, polyoxypropylene , polyvinylacetate, polyoxybutylene, polyisoprene, polybutadiene, polyvinylchloride, polyalkylacrylate (PAA), polyalkylmethacrylate, polyacrylonitrile, polypropylene, PTHF, polymethacrylates, polyacrylates, polysulfones, polyvinylethers, and poly(propylene oxide), and copolymers thereof.

The hydrophobic segment preferably contains a predominant amount of hydrophobic monomers. A hydrophobic monomer is a monomer that typically gives a homopolymer that is insoluble in water and can absorb less than 10% by weight of water.

Suitable hydrophobic monomers are C1–C18 alkyl and C3–C18 cycloalkyl acrylates and methacrylates, C3–C18 alkylacrylamides and -methacrylamides, acrylonitrile, methacrylonitrile, vinyl C1–C18 alkanoates, C2–C18 alkenes, C2–C18 haloalkenes, styrene, (lower alkyl)styrene, C4–C12 alkyl vinyl ethers, C2–C10 perfluoro-alkyl acrylates and methacrylates and correspondingly partially fluorinated acrylates and methacrylates, C3 through C12 perfluoroalkylethylthiocarbonylaminoethyl acrylates and methacrylates, acryloxy- and methacryloxyalkylsiloxanes, N-vinylcarbazole, C1 through C12 alkyl esters of maleic acid, fumaric acid, itaconic acid, mesaconic acid, vinyl acetate, vinyl propionate, vinyl butyrate, vinyl valerate, chloroprene, vinyl chloride, vinylidene chloride, vinyltoluene, vinyl ethyl ether, perfluorohexyl ethylthiocarbonylaminoethyl methacrylate, isobornyl methacrylate, trifluoroethyl methacrylate, hexa-fluoroisopropyl methacrylate, hexafluorobutyl methacrylate, tristrimethylsilyloxysilylpropyl methacrylate (TRIS), and 3-methacryloxypropylpentamethyldisiloxane.

In one embodiment, the hydrophobic polymer is one which displays a relatively high oxygen diffusion rate there through, such as, but not limited to, polysiloxanes, perfluoroalkyl ethers, specific unsaturated polymers, and polysulfones. In one embodiment, the hydrophobic polymer is a polysiloxane block having terminal alkylene groups.

In another embodiment, the hydrophobic polymer includes a perfluoroalkyl-polyether block. In another embodiment, the hydrophobic polymer includes an unsaturated polymer, such as a polymer of a conjugated aliphatic or alicyclic diene, which may be substituted by halogen or lower alkyl, a polymer of an alkyne or dialkyne, which may be substituted by lower alkyl or trimethylsilyl, a copolymer of a conjugated diene and a hydrophilic or hydrophobic vinylic monomer, and also partially hydrated derivatives of these compounds.

Specific examples of preferred polymers of conjugated dienes are cis-, trans-, iso- or syndiotactic poly-1,2-butadiene, poly-1,4-butadiene or polyisoprene, polypentenamer, polychloroprene and polypiperylen. Preferred examples of copolymers are butadiene- or isoprene-copolymers with hydrophilic or hydrophobic vinylic monomers, such as acrylonitrile, styrene, acrylic acid or hydroxyethylmethacrylate. An example of a polyalkyne is poly-1-trimethylsilyl-propyne. Especially preferred unsaturated polymers are syndiotactic poly-1,2-butadiene, poly-1,4-butadiene and polyisoprene. An especially preferred unsaturated polymer is poly-1-trimethylsilyl-propyne. Another especially preferred unsaturated polymer is poly-1,4-butadiene.

The hydrophobic polymer may include a single type of polymer or more than one type of polymer, such as two or more of those discussed above. The mean molecular weight of one segment B is in the range from about 500 to about 50,000, preferably in the range from about 800 to about 15,000, more preferably in the range of about 1,000 to 12,000, particularly preferably in the range from about 5,000 to about 12,000.

In addition to the hydrophobic segment B, the amphiphilic segmented copolymer includes at least one segment A which includes at least one hydrophilic polymer, such as, but not limited to, polyoxazoline, polyethylene glycol, polyethylene oxide, polyvinyl alcohol, polyvinylpyrrolidone, polyacrylamide, poly(meth)acrylic acid, polyethylene oxide-co-polypropyleneoxide block copolymers, poly (vinylether), poly(N,N-dimethylacrylamide), polyacrylic acid, polyacyl alkylene imine, polyhydroxyalkylacrylates such as hydroxyethyl methacrylate (HEMA), hydroxyethyl acrylate, and hydroxypropyl acrylate, polyols, and copolymeric mixtures of two or more of the above mentioned polymers, natural polymers such as polysaccharides and polypeptides, and copolymers thereof, and polyionic molecules such as polyallylammonium, polyethyleneimine, polyvinylbenzyltrimethylammonium, polyaniline, sulfonated polyaniline, polypyrrole, and polypyridinium, polythiophene-acetic acids, polystyrenesulfonic acids, zwitterionic molecules, and salts and copolymers thereof.

The hydrophilic segment preferably contains a predominant amount of hydrophilic monomers. A hydrophilic comonomer is a monomer that typically gives a homopolymer that is soluble in water or can absorb at least 10% by weight of water.

Suitable hydrophilic monomers are hydroxyl-substituted lower alkyl acrylates and methacrylates, acrylamide, methacrylamide, (lower alkyl) acrylamides and methacrylamides, N,N-dialkyl-acrylamides, ethoxylated acrylates and methacrylates, polyethyleneglycol-mono methacrylates and polyethyleneglycolmonomethylether methacrylates, hydroxyl-substituted (lower alkyl) acrylamides and methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)-(where the term amino also includes quaternary ammonium), mono(lower alkylamino)(lower alkyl) and di(lower alkylamino)(lower alkyl) acrylates and methacrylates, allyl alcohol, 3-trimethylammonium 2-hydroxypropylmethacrylate chloride (Blemer,QA, for example from Nippon Oil), dimethylaminoethyl methacrylate (DMAEMA), dimethylaminoethylmethacrylamide, glycerol methacrylate, and N-(1,1-dimethyl-3-oxobutyl) acrylamide.

In one embodiment, the segment A includes a polymer displaying a relatively high water or ion diffusion rate there through. Specific examples of hydrophilic monomers from which such polymers can be made are cyclic imino ethers, vinyl ethers, cyclic ethers including epoxides, cyclic unsaturated ethers, N-substituted aziridines, β-lactones and β-lactames. Further suitable monomers include ketene acetals, vinyl acetals and phosphoranes. Suitable cyclic imino ethers include 2-oxazoline. If a 2-oxazoline having an alkenyl group in 2 position is used as hydrophilic monomer, a polymerizable unsaturated group is provided within segment A (in a side chain) of the amphiphilic segmented copolymer to serve as the polymerizable unsaturated group necessary for the final polymerization to obtain a polymeric product or as an additional polymerizable unsaturated group which offers the possibility of direct crosslinking in the preparation of the polymer. The most preferred cyclic imino ether is 2-methyloxazoline. The most preferred vinyl ethers are methyl vinyl ether, ethyl vinyl ether and methoxy ethyl vinyl ether.

The mean molecular weight of one segment A is in the range from about 500 to about 50,000, preferably in the range from about 800 to about 15,000, more preferably in the range of about 1,000 to 12,000, particularly preferably in the range from about 5,000 to about 12,000.

B. Preparation of the Amphiphilic Copolymer

The segments A and B are linked together through a bond that may be hydrolyzable or non-hydrolyzable. A non-hydrolyzable bond is a covalent bond that is not cleaved by an ordinary aqueous or solvent hydrolysis reaction, e.g. under acidic or basic conditions. Specific bonds that are hydrolyzable within the meaning of the term are well known to those skilled in the art.

A non-hydrolyzable bond between segments A and B in the amphiphilic segmented copolymer can be formed by polymerizing a suitable hydrophilic monomer (from segment A) in the presence of a suitably functionalized hydrophobic monomer (from segment B) such that a block of units of the hydrophilic monomer grows from the site of functionalization of the hydrophilic monomer or, alternatively by polymerizing a suitable hydrophobic monomer in the presence of a suitably functionalized hydrophilic monomer such that a block of units of the hydrophobic monomer grows from the site of functionalization of the hydrophilic monomer.

The functionalized segment is also called a macroinitiator. Suitable macroinitiators include a thermally or photochemically activatable cationic or anionic groups, or a thermally or photochemically activatable radical initiator group. Anionic polymerization, polycondensation, and polyaddition can also be used. Specific examples of preferred photochemically activatable cationic initiator groups are triflate (—O—$SO_2$—$CF_3$), —I(iodide), —O-mesyl, —O-tosyl, and —Cl+ $AgSbF_6$. The most preferred initiator group is the triflate group. The initiator group is linked to the starting segment in a way that provides a covalent non-hydrolyzable bond between the terminal group of the starting segment and the first monomer forming the growing segment that is attached to the starting segment during the graft copolymerization for preparing the amphiphilic segmented copolymer. Grafting means that polymer chains are grown from a monomer either in terminal or in pendant position onto another preformed polymer.

The initiator group may be introduced into a preformed polymer in a suitable way, for example through linkage of cationic or thermal initiator groups to functional groups present on the starting monomer. Only the latter method is suitable for providing pendent initiator groups. Preferred triflate groups can be introduced by reaction of terminal or pendent functional hydroxyl groups with activated triflic acid derivatives such as $(CF_3SO)_2O$.

A degradable bond between the A segment and the B segment can be used so that the membrane can be degraded. Degradable bonds within the A or B segment can also be used. Degradable regions can be constructed from polymers or monomers using linkages susceptible to biodegradation. Biodegradable bonds, such as enzymatically degradable bonds, can also be used. Degradability can be imparted by inclusion of a single degradable linkage or a degradable region made of more than one degradable linkage. The terms degradable linkage and degradable region are used interchangeably hereinafter.

The degradable region is preferably degradable under in vivo conditions. For example, a biodegradable region may be a hydrolyzable region, such as made from a polymer or oligomer of glycolide, lactide, $\epsilon$-caprolactone, other hydroxy acids, or other biologically degradable polymer that yields materials that are non-toxic or present as normal metabolites in the body. Preferred poly($\alpha$-hydroxy acid)s are poly(glycolic acid), poly(DL-lactic acid), and poly(L-lactic acid). Other useful materials include poly(amino acids), poly(anhydrides), poly(orthoesters), poly(phosphazines) and poly(phosphoesters). Polylactones such as poly($\epsilon$-caprolactone), poly($\delta$-valerolactone), and poly($\gamma$-butyrolactone), for example, are also useful. The biodegradable region may have a degree of polymerization ranging from one up to values that would yield a product that was not substantially water soluble. Thus, monomeric, dimeric, trimeric, oligomeric, and polymeric regions may be used.

Accordingly, the amphiphilic segmented copolymers may consist in one embodiment of one segment A and one segment B (A—B-type, diblock), or of one segment A and two segments B attached to its termini (B—A—B-type, triblock), or may have a comb-type structure wherein several segments B are pendent from one segment A, which may further carry one or two terminal segments B). In another embodiment, the amphiphilic segmented copolymers may consist of one segment B and two segments A attached to its termini (A—B—A-type, triblock). In another embodiment, the amphiphilic segmented copolymers may have a comb-type structure wherein several segments A are pendent from one segment B, which may further carry one or two terminal segments A. Preferably, the copolymer is an ABA triblock copolymer.

It is also possible to change the monomer during graft copolymerization such that, for example, first hydrophilic segments A are grown on a preformed hydrophobic segment B and then hydrophobic segments B' are attached to the termini of the earlier prepared segments A. Also a different hydrophilic monomer may be used to produce a different hydrophilic segment A' at the termini of the hydrophilic segments A. Again, other embodiments of the amphiphilic segmented copolymers may be produced starting from a functionalized hydrophilic segment A.

The polymer that makes up the starting segment (A or B) usually has a number average molecular weight Mn in the range from about 500 to about 50,000, preferably in the range from about 800 to about 15,000, more preferably in the range of about 1,000 to 12,000, particularly preferably in the range from about 5,000 to about 12,000. The length of the one or more segments A, B, A', or B' which are to be graft copolymerized on the starting segment can be easily controlled by controlling the amount of monomer (hydrophilic or hydrophobic) which is added for the graft copolymerization. In this way the size of the segments and their ratio can easily be controlled.

The amphiphilic segmented copolymers can be prepared in the presence or absence of a solvent. It is advantageous to use a substantially inert solvent, i.e. one that does not participate in the reaction. Suitable examples are halogenated hydrocarbons, such as chloroform or methylene chloride, bipolar aprotic solvents, such as acetonitrile, acetone, dimethylformamide (DMF) or dimethyl sulfoxide (DMSO), hydrocarbons, such as toluene or xylene, and pyridine or N-methylmorpholine, and mixtures thereof.

In the preparation of the amphiphilic segmented copolymers of the invention, the reaction temperature can be, for example, from –60° C. to 150° C., preferably from 0° C. to 80° C. The reaction times are in the range from about 15 minutes to 7 days, preferably in the region of about 2 to 48 hours. If necessary, the reaction is carried out under argon or nitrogen as protective gas. A suitable catalyst, for example dibutyltin dilaurate (DBTDL), is added in the urethane-forming terminal functionalizing reaction.

C. Polymerization Groups

The segmented copolymers may already contain polymerizable groups in the hydrophobic and/or hydrophilic segments, e.g. if a hydrophobic segment B comprises a dienepolymer like polybutadiene or polyisoprene, or if the monomer used for making a hydrophilic segment comprises an unsaturated side chain, for example 2-allyl-oxazoline. Whether or not present, it is possible to introduce polymerizable groups by suitable reactions, e.g. at the end of or also pendent from the growing segments. For this purpose, the graft polymerization of the growing segment may be terminated after a suitable chain length is reached and the initiator group present at the chain end capped, for example, either by using specific reagents such as hydroxy styrene, allyl alcohol, HEMA, propargyl alcohol, allyl amines and propargyl amine, or by using KOH/EtOH or primary amines leaving —OH or —NH— groups or unsaturated groups at the end of the growing segment. Hydroxyl groups may also be introduced into the copolymers by employing suitable comonomers in the graft copolymerization, e.g. 2-hydroxy-alkyloxazolines. The hydroxyl or —NH— groups may then be reacted, e.g. with an isocyanate carrying a polymerizable unsaturated group. Preferred examples of such bifunctional compounds are 2-isocyanatoethyl methacrylate (IEM), which is especially preferred, and vinyl isocyanate, allyl isocyanate, acryloyl isocyanate, styrene isocyanate, vinyl benzyl isocyanate, propargyl isocyanate, and (meth)acrylic anhydride. Other polymerizable groups can be introduced by methods known to those skilled in the art.

Any type of polymerization/crosslinking can be used. Examples include photopolymerization, redox polymerization, anionic polymerization, condensation reactions, addition reactions, and chain polymerization reactions.

D. Additional Monomers

In the preferred polymeric product, the proportion by weight of the amphiphilic segmented copolymer is in the range from 100 to 50%, in particular in the range from 100 to 80%, preferably in the range from 100 to 90%, based on the total polymeric product. The polymeric product may be obtained by direct further thermal or photochemical polymerization or crosslinking reaction of the amphiphilic segmented copolymer without the addition of comonomers in the presence of a suitable initiator. However, in some cases, it may be preferable to include a comonomer. Types of comonomers that may be desired include hydrophobic or hydrophilic comonomers, or cationic or anionic comonomers. It may also be desirable to include a comonomer that contains a specific functional group, such as a crosslinkable group, or a group that has a particular affinity for a molecule to be incorporated into or onto the membrane, as discussed below. Suitable hydrophobic and hydrophilic comonomers include those discussed above.

The comonomers can be included either within the amphiphilic polymer network, or crosslinked as an interpenetrating or semi-interpenetrating network with the amphiphilic polymer. Crosslinking may be achieved with the addition of a comonomer and/or a crosslinking agent, for example, a polyunsaturated comonomer.

E. Crosslinking Agents

A polymer network can, if desired, be reinforced by addition of a crosslinking agent, for example, a polyunsaturated comonomer. A crosslinked polymeric product including the product of the polymerization and crosslinking reaction of an amphiphilic segmented copolymer, can also be formed, if desired, with at least one vinylic comonomer and with at least one crosslinking agent. Crosslinking can be achieved by a number of different means, such as but not limited to, free radical crosslinking, redox crosslinking, and salt crosslinking.

Examples of suitable crosslinking agents include allyl methacrylate, lower alkylene glycol dimethacrylate, poly (lower alkylene) glycol dimethacrylate, lower alkylene dimethacrylate, divinyl ether, divinyl sulfone, di- and trivinylbenzene, trimethylolpropane trimethacrylate, pentaerythritol tetramethacrylate, bisphenol A dimethacrylate, methylenebis(meth)acrylamide, triallyl phthalate and diallylphthalate, $\alpha$-$\omega$-bis (methacryloxyalkyl)-oligosiloxanes such as bis(methacryloxypropyl) tetramethyldisiloxane, and perfluoroalkyl- or perfluoroalkylether-bismethacrylates.

The amount of crosslinking agent used is expressed in a proportion by weight based on the total polymer and is in the range from 20 to 0.05%, in particular in the range from 10 to 0.1%, preferably in the range from 5 to 0.1%.

F. Crosslinking Initiators

The polymeric products are crosslinked in a manner known in the art from the corresponding monomers (the term monomer here also including an amphiphilic segmented copolymer) by a polymerization reaction customary to the person skilled in the art.

In the case of monomers that can be crosslinked with free radical crosslinking, a mixture of monomers is typically warmed with addition of a free-radical former. Examples of such free-radical formers are azoisobutyronitrile (AIBN), potassium peroxodisulfate, dibenzoyl peroxide, hydrogen peroxide, and sodium percarbonate. If, for example, the compounds are warmed, free radicals form with homolysis, and can then initiate polymerization.

A polymerization reaction may be carried out using a photoinitiator that can initiate free-radical polymerization and/or crosslinking. Examples of suitable photoinitiators include benzoin methyl ether, 1-hydroxycyclohexylphenyl ketone, and Darocure and Irgacure products, preferably Darocure 1173® and Irgacure 2959®. Also suitable are reactive photoinitiators, which can be incorporated, for example, into a macromer, or can be used as a specific comonomer. Examples are described in European Patent No. EP 0 632 329. The photopolymerization can then be initiated by actinic radiation, for example light, in particular UV light having a suitable wavelength. The spectral requirements can, if necessary, be controlled appropriately by addition of suitable photosensitizers.

The polymerizable regions may be polymerizable by photoinitiation by free radical generation, most preferably in the visible or long wavelength ultraviolet radiation. Polymerizable regions are acrylates, diacrylates, oligoacrylates, dimethacrylates, oligomethoacrylates, or other biologically acceptable photopolymerizable groups. A preferred tertiary amine is triethanol amine.

Useful photoinitiators are those that can be used to initiate by free radical generation polymerization of the macromers without cytotoxicity and within a short time frame, minutes at most and most preferably seconds. Preferred dyes as initiators of choice for LWUV initiation are ethyl eosin, 2,2-dimethoxy-2-phenyl acetophenone, other acetophenone derivatives, and camphorquinone. In all cases, crosslinking and polymerization are initiated among copolymers by a light-activated free-radical polymerization initiator such as 2,2-dimethoxy-2-phenylacetophenone or a combination of ethyl eosin ($10^{-4}$–$10^{-2}$ milliM) and triethanol amine (0.001 to 0.1 M), for example.

The choice of the photoinitiator is largely dependent on the photopolymerizable regions. For example, when the macromer includes at least one carbon-carbon double bond, light absorption by the dye causes the dye to assume a triplet state, the triplet state subsequently reacting with the amine to form a free radical that initiates polymerization. Preferred dyes for use with these materials include eosin dye and initiators such as 2,2-dimethyl-2-phenylacetophenone, 2-methoxy-2-phenylacetophenone, and camphorquinone. Using such initiators, copolymers may be polymerized in situ by long wavelength ultraviolet light or by laser light of about 514 nm, for example. Lasers may be used to polymerize any nanospheres from a photopolymerizable solution, due to the precise control that can be achieved with the lasers. It is thus possible to make nanospheres as described herein without inclusion of the amphiphilic polymers.

Initiation of polymerization is accomplished by irradiation with light at a wavelength of between about 200–700 nm, most preferably in the long wavelength ultraviolet range or visible range, 320 nm or higher, most preferably about 514 nm or 365 nm. The light-sensitive free-radical polymerization initiator may be a single compound (e.g. 2,2-dimethoxy-2-phenyl acetophenone) or a combination of a dye and a cocatalyst (e.g., ethyl eosis and triethanol amine).

G. Solvents

Polymerization/crosslinking can be carried out in the presence or absence of a solvent. Suitable solvents are all solvents which dissolve the monomers used, for example, water, alcohols such as lower alkanols like ethanol or methanol, carboxamides such as dimethylformamide, dipolar aprotic solvents such as dimethyl sulfoxide or methyl ethyl ketone, ketones such as acetone or cyclohexanone, hydrocarbons such as toluene, ethers such as THF, dimethoxyethane or dioxane, halogenated hydrocarbons such as trichloroethane, and mixtures of suitable solvents such as mixtures of water and an alcohol, for example, a water/ethanol or water/methanol mixture.

II. Planar Membranes Formed from the Amphiphilic Copolymers

Freestanding films from the amphiphilic copolymers can be made adopting the standard procedure applied with conventional low molecular weight lipids [Mueller, P., Rudi, D. P., Tien, H. T., Wescott., W. C., *J Phys. Chem. B*, 1963, 67, 534]. This method is generally termed the "black membrane" process because the membranes appears black in reflected light as it thins out during its preparation.

Generally, the copolymer molecules are dissolved in a solvent, such as chloroform and/or toluene at a low concentration (about 1 to 10% by weight). The solution is painted over a pinhole formed in a substrate, such as a polyethylene or Teflon™ substrate or a loop, such as made out of metal, polyethylene, hair, or Teflon™ is dipped in the polymer solution. The substrate or loop is initially in water or buffer or is placed into water or buffer. The polymer organizes into its most stable structure, which is a bilayer membrane, with the hydrophilic portions towards the aqueous phase and the hydrophobic portions towards the center.

The strength and other characteristics of the membrane can be tested by methods known in or adopted from the art. A well-established technique to quantify viscoelastic properties of planar lipid membranes is to apply controlled forces e.g. via a short electric field pulse [Diederich, A., Strobel, M., Meier, W., Winterhalter, M.,*J Phys. Chem. B*, 1999, 103, 9, 1402]. Electric field pulses are used to charge the membrane causing an electric stress inside the bilayer. Above a critical voltage rupture of the membrane is induced and a fast discharge across the defect is observed. An analysis of the critical voltage gives information about the energy barrier of the membrane against rupture. An analysis of the discharge kinetics allows conclusion on the kinetics of defect widening and the underlying physical forces.

In an alternative procedure for preparing freestanding films, both compartments of the chamber are filled with a small amount of aqueous buffer. The surface must be below the hole in the septum. The organic polymer solution (in toluene or chloroform) is spread on the surface of the aqueous phase in each compartment. After the solvent has evaporated, the level in the compartments is raised over the hole where the polymer monolayers form a bilayer membrane across the aperture (M. Montal, P. Mueller, Proc. Natl. Acad. Sci. USA, 69, 3561–3566 (1972)).

Other methods of making planar membranes can also be used such as the Langmuir-Blodgett process (LB process), which is known by those skilled in the art.

In general, planar membranes with a thickness ranging from about 1 to 100 nm, for example on the order of about 10 nm can be prepared from a triblock amphiphilic copolymer. Stable membranes with areas from about 10 nm$^2$ to 10 cm$^2$, generally up to about 1 mm$^2$ can be made.

The triblock copolymer can have polymerizable groups at both chain ends or internal. These polymerizable groups can be polymerized after the formation of the self-assembled membrane. The mechanical properties of the membranes, as characterized by short electric fields, are significantly more cohesive than lipid bilayers, as seen by the higher critical voltages required for rupture. The polymerization further increases the stability of the films. Further crosslinking of polymerized membranes can be achieved by incorporating crosslinkable groups into the copolymers, such as crosslinkable groups in the hydrophobic segments.

III. Incorporation of Molecules into the Planar Membrane

Many different types of molecules can be inserted into the planar membranes, including therapeutic, diagnostic, or prophylactic agents (collectively referred to as "active agent"). Examples of active agents include peptides and proteins, lipids, polysaccharides, inorganic molecules, organic molecules, and nucleic acids. Hydrophobic or amphiphilic molecules are more easily incorporated into the membrane. The amount of the molecule that can be incorporated will depend on many factors, including its molecular weight, hydrophobicity, and charge, and can be readily determined by one of skill in the art. In one embodiment, the molecule is a biological molecule, such as a protein, and especially preferred are membrane proteins, or proteins that typically exist within a biological membrane.

Examples of membrane proteins include general transport proteins such as the bacterial porin OmpF, specific transport proteins such as maltoporin and LamB, active transport proteins such as Na—K— pump, phosphotransferases, and bacteriorrhodopsin, and immunoglobulins, such as IgG, T-cell receptors, CD4, CD8, and N-CAM.

The molecule can be incorporated during formation of the membrane, by including it in the polymer solution. The molecule can also or alternatively be incorporated into the membrane after the membrane has been formed. In one embodiment, a biological molecule is inserted into the membrane after the membrane has been formed by including the molecule in a solution placed on one side of the membrane. Insertion of the molecule into the membrane can often be accelerated by applying a potential across the membrane.

Molecules can also be incorporated into or onto the membrane in ways other than direct insertion into the membrane. For example, a reactive group on the segmented polymer, such as a methacrylate end group, could be used to react with a reactive group (e.g. an amino or thiol) on a protein. This would lead to the formation of a covalent bond between the membrane and the protein. As a result the protein would be immobilized at the surface of the membrane rather than within the membrane.

The molecule can be incorporated into the membrane before or after the membrane is polymerized and/or crosslinked, although in some cases, a large molecule may be ejected from the membrane during polymerization or crosslinking.

The compositions and methods described herein will be better understood with reference to the non-limiting examples described below.

EXAMPLES

The synthesis of a poly (2-methyloxazoline)-block-poly (dimethylsiloxane)-block-poly (2-methyloxazoline) (PMOXA-PDMS-PMOXA) triblock copolymer carrying polymerizable groups at both chain ends is described in Example 1. The synthesis of this material is also described in Nardin, C., Hirt, T., Leukel, J., Meier, W., *Langmuir*, 2000, 16, 1035.

The formation of freestanding planar membranes from the triblock copolymer is described in Example 2, as well as subsequent polymerization of the copolymer. The physical properties of the polymer films before and after polymerization are characterized in Example 3 and the results compared with conventional black lipid membranes.

The incorporation of a protein into a planar membrane is described in Example 4.

Example 1
Synthesis of PMOXA-PDMS-PMOXA Diblock and Triblock Copolymers.

Bifunctional Poly (Dimethylsiloxane)

In a 250 mL round bottom two-necked flask with a Soxhlet extractor (filled with molecular sieve (4 A)), a condenser and a septum on the second ground joint, 34.2 g (6.34 mmol) α-ω-bis (3-hydroxypropyl)-polydimethylsiloxane (I<15, Wacker Chemie, additionally purified over a thin-film evaporator; Mw=5400 g mol$^{-1}$) were dissolved in 90 mL hexane and distilled under reflux for 17 h in a nitrogen atmosphere. After this drying procedure, the solution still contained 21 ppm water. Subsequently, the solution was concentrated to 60 mL hexane, cooled to 0° C. and 3.6 g (45.5 mmol) of dry pyridine were added. Then, 12.4 g (43.9 mmol) trifluoromethane sulfonic acid anhydride were added over 15 minutes and the mixture was stirred for another 30 min at a temperature of 0° C. After the addition of 20 mL chloroform (water content <10 ppm), the resulting suspension was filtered under vacuum using a G4 glass filter funnel. The solvent was evaporated under high vacuum.

The yield was 21.5 g of oil of orange color. This oil was in turn dissolved in 40 mL of dry hexane, activated charcoal was added, and the mixture was then stirred for about 2 min and filtered again. After evaporation of the solvent, the yield was 19.0 g of clear colorless oil. $^1$H-NMR (CDCL$_3$, 250 MHz): 0 ppm (CH$_3$—Si), 0.5 ppm (—CH$_2$—CH$_2$—Si), 1.8 ppm (—CH$_2$CH$_2$—CH$_2$—), 4.4 ppm (CF$_3$SO$_3$CH$_2$—CH$_2$—). Functionality >95% based on the $^1$H-NMR data.

Poly (2-methyloxazoline)-block-poly (dimethylsiloxane)-block-poly (2-methyloxazoline) (PMOX-PDMS-PMOXA) Triblock Copolymer with Free Hydroxy End Groups 5.04 g (59.2 mmol) freshly distilled 2 methyl-2-oxazoline and 8.05 g (1.4 mmol) of the bifunctional PDMS were added to 15 mL 1.2-dichloroethane (water content <5 ppm) at room temperature. The solution was then stirred for 1.5 h and subsequently heated to 40° C. After 48 hr, the solution was cooled again to room temperature and 5.5 mL of a 0.5 M KOH solution in ethanol were added. The resulting solution was stirred for one hour and subsequently the solvent was evaporated under high vacuum. The yield was 12.0 g of colorless solid polymer. $^1$H-NMR (CDCL$_3$, 250 MHz): 0 ppm (CH$_3$—Si), 2.0–2.1 ppm (CH$_3$CON<), 3.3–3.5 ppm (>N—CH$_2$—CH$_2$—N<). Functionality >95% according to OH titration (>0.4 mEq g$^{-1}$). GPC in THF revealed a molecular weight of the triblock copolymer of $M_n$=9000 g mol$^{-1}$ and a polydispersity of $M_w/M_n$=1.7. Consequently, the molecular weight of the two poly-2-methyloxazoline blocks was $M_n$=1800 gmol$^{-1}$, respectively.

PMOXA-PDMS-PMOXA Triblock Copolymers with Polymerizable End Groups

In a round bottom flask, 7.68 g (1.32 mmol) of the hydroxy-functionalized PMOXA-PDMS-PMOXA triblock copolymer were dissolved at room temperature in 20 mL dry ethyl acetate (water content <10 ppm). To this solution were added 420 mg (2.7 mmol) of 2-isocyanato-ethylmethacrylate (IEM) and about 40 mg dibutyltin dilaureate. The solution was stirred for 48 h in the absence of light. Afterwards, the solvent was evaporated under high vacuum for 5 h at a temperature of 0C. The raw product was purified using ultrafiltration in a water/ethanol mixture to remove low molecular weight impurities. 6.89 g of the colorless solid polymer were obtained. $^1$H-NMR (CDCL$_3$, 250 MHz): 0 ppm (CH$_3$—Si), 2.0–2.2 ppm (CH$_3$—CO), 3.3–3.5 ppm (>N—CH$_2$—CH$_2$—N<, >N—CH$_2$—CH$_2$—O<), 5.5 ppm (CH$_2$=), 6.1 ppm (CH$_2$=). Functionality >95% according to $^1$H-NMR.

The molecular weight (Mw) of the material was 9000 gmol$^{-1}$ and the molecule includes a flexible hydrophobic PDMS middle block of 5400 gmol$^{-1}$ and two hydrophilic PMOXA blocks each of 1800 gmol$^{-1}$. The polydispersity was determined to be $M_w/M_n$=1.7.

Example 2

Preparation of a Planar Membrane from PMOXA-PDMS-PMOXA.

A freestanding film from the PMOXA-PDMS-PMOXA triblock copolymer with polymerizable end groups was made adopting the standard procedure applied with conventional low molecular weight lipids.

The end-group functionalized triblock copolymer was dissolved in chloroform (2% by weight polymer). This solution was diluted with toluene in order to obtain a clear, homogeneous one % by weight polymer solution. About 1 μL was used for prepainting the Teflon® surrounding the hole. After 20 minutes for drying, both chambers were filled with a standard buffer containing 1 M KCl. 1 mM CaCl$_2$ and 10 mM Tris (hydroxymethyl)-aminomethane (Tris) adjusted to pH 7.4. The membrane was made using the membrane forming solution of the triblock copolymer by adding about 2 μL on a Teflon® loop and smearing it across the prepainted hole. Within a few seconds the film started to thin out.

The polymerization of the copolymer membranes was achieved by irradiating the freestanding film for 5 min with an UV lamp. Previous investigations on the polymerization of the functionalized triblock copolymers in vesicles [Nardin, C., Hirt, T., Leukel, J., Meier, W., *Langmuir*, 2000, 16, 1035] and lyotropic liquid crystalline phases [Hirt, T., Baron, R. C., Lohman, D., Meier, W., WO 99/12059; Meier, W., *Macromolecules*, 1998, 31, 2212] revealed a conversion of more than 90% of the methacrylate end-groups under these conditions.

All experiments were performed at room temperature (22±2° C.).

Freestanding films of functionalized PMOXA-PDMS-PMOXA copolymer molecules were obtained. The block copolymer macromolecules are soluble in a few organic solvents including chloroform. However, a chloroform based membrane forming solution phase separated too quickly in the present case. Addition of toluene slowed down the process and yielded the reproducible formation of giant stable freestanding films. Depending on the set-up, stable films with areas up to about 1 mm$^2$ were obtained. The one used in the present experiments typically yielded an area of 0.02 mm. This smaller area has the advantage that the thinning of the films, observed through the quasi instantaneous evanescence of interference colors, is faster.

Example 3

Characterization of a Planar Membrane from PMOXA-PDMS-PMOXA.

Table 1 reports the characteristics of the formed membranes and compares those characteristics with those reported for a typical lipid membrane. Wilhelm, C., Winterhalter, M., Zimmerman, U., Benz, R., *Biophys. J.*, 1993, 64, 121; Benz, R., Janko, K., Biochim. Biophys. Acta, 1976, 455, 721; Dilger, Benz, *J Membr. Biol.*, 1985,85, 181.

TABLE 1

Membrane Characteristics

| Property | Lipid membrane-reported | Non-polymerized amphiphilic polymer membrane | polymerized amphiphilic polymer membrane |
|---|---|---|---|
| C- Membrane capacitance (nF) | 0.07 | 0.05 | 0.05 |
| d- Thickness (nm) | 4–5 | 10 | 10 |
| Area (mm$^2$) | 0.02 | 0.02 | 0.02 |
| U$_c$- Breakdown voltage (V) | 0.5 V | 1.0 ± 0.2 | 1.5 ± 0.2 V |
| fast rupture velocity (ms$^{-1}$) | 0.02–0.06 | 1 | 5 |
| delay time between the pulse and the beginning of the membrane rupture (μs) | 50–100 | 50 | 25–34 |

Due to the finite contact angle at the edge of the Teflon rim, the interface is subjected to a surface tension that will favor opening of pores in the membrane. However, to create a pore requires the formation of an edge. This will provide the energy barrier. Due to the longer hydrophobic part in comparison to lipids, the cohesion energy between the polymerizable triblock copolymer molecules is expected to be higher than the one between conventional low molecular weight lipids. To quantify this effect a set of experiments was devoted to characterize the stability of the triblock copolymer membranes.

To control the quality of the PMOXA-PDMS-PMOXA triblock copolymer freestanding film, the capacitance was determined by charging the membrane and recording the relaxation across a defined resistance. A voltage pulse of 500 mV with a rectangular pulse of 10 µs duration using a fast pulse generator (DS 345.30 MHz Synthesized Function Generator, Stanford Research System) was applied. This amplitude is below the critical one leading to rupture. The value of the capacitance is calculated from the RC-time constant of the exponential discharge process of the membrane across the 10 MΩ resistance of the passive oscilloscope probe (See FIG. 1 for a schematic of the instrumentation).

Raising the applied voltage in 20 mV steps and applying several pulses per step until the membrane disrupts irreversibly induces a single defect. The presented technique charges the membrane capacitor and after the voltage pulse, the transmembrane voltage discharges immediately which avoids high field strengths.

Figure 2:
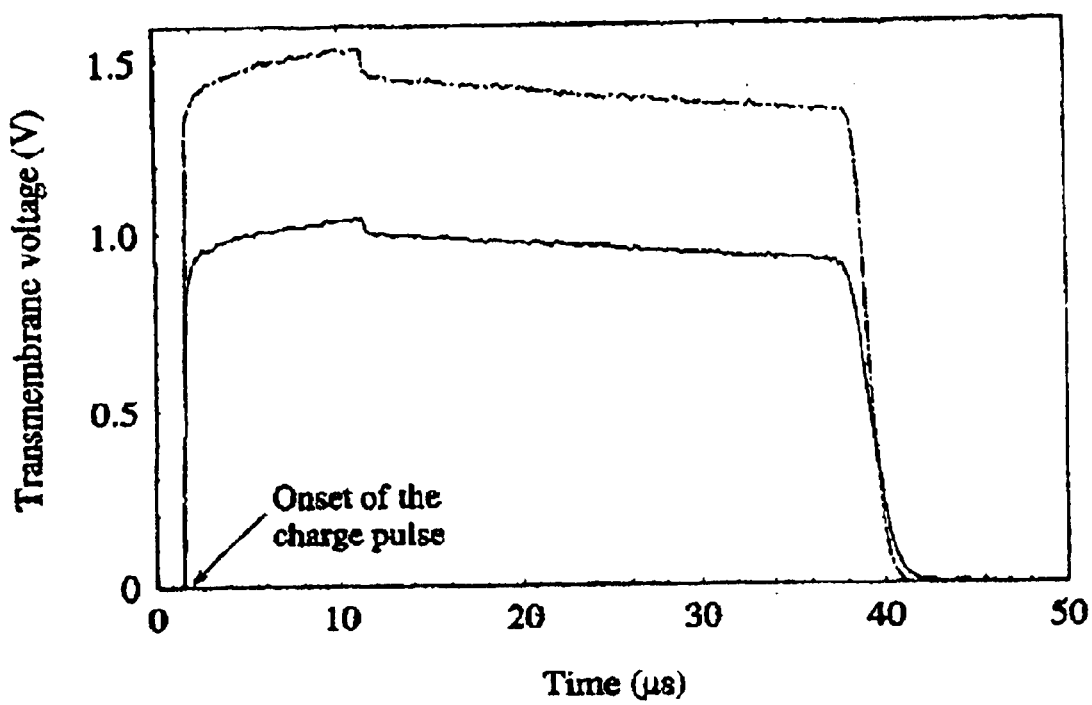
FIG. 2 is a representative time course of the transmembrane voltage during electric field induced irreversible rupture of a poly (2-methyloxazoline)-block-poly (dimethylsiloxane)-block-poly (2-methyloxazoline) (PMOXA-PDMS-PMOXA) copolymer membrane, where the solid line indicates a non-polymerized membrane and the dashed line indicates a polymerized membrane.

FIG. 2 shows a typical time course of the transmembrane voltage after a short charge pulse of 10 µs. The transmembrane voltage shows an exponential decay caused by the discharge through the 10 MΩ resistor of the passive oscilloscope probe. This relaxation is followed by a superexponential decrease indicating the onset of the irreversible rupture of the membrane.

Carefully raising the voltage amplitude of the pulses leads to a sudden drop in the transmembrane voltage (FIG. 2). Initially the defect area is negligible compared to the total area and the membrane capacitance can be considered as constant. A defect free membrane is a perfect insulator. Under the chosen conditions, the measured conductance is due to the 10 MΩ resistor of the passive oscilloscope probe and possible defects in the membrane occurring after rupture. After initiating the irreversible rupture the defect formation becomes the major source of conductance.

Figure 3:
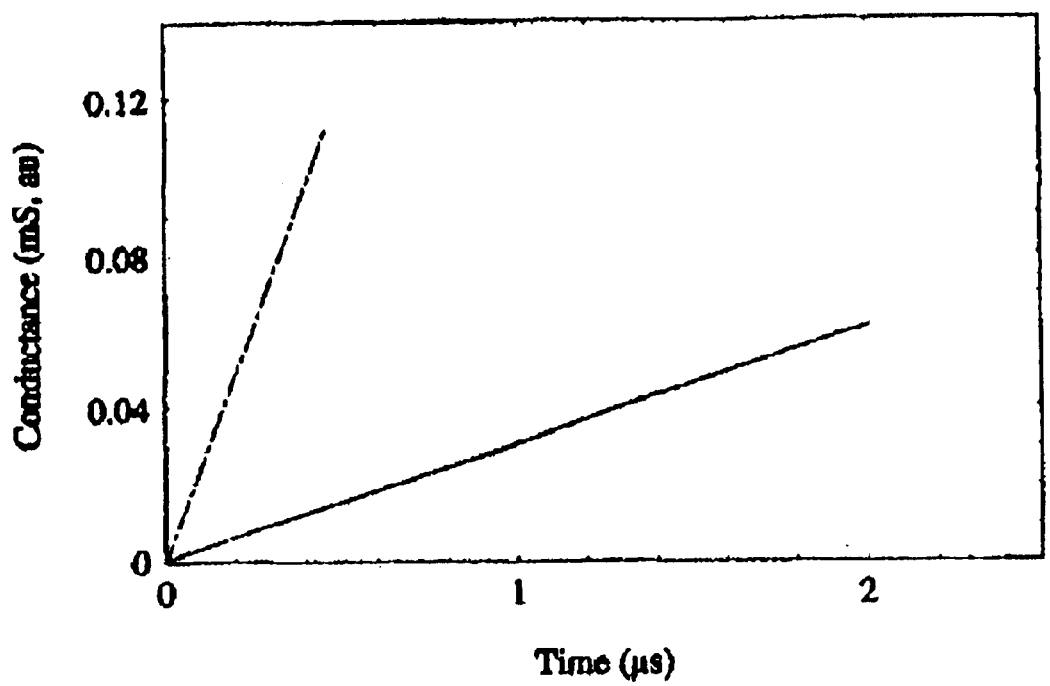
FIG. 3 is a representative time course of the conductance of a PMOXA-PDMS-PMOXA copolymer membrane, where the solid line indicates a non-polymerized membrane and the dashed line indicates a polymerized membrane.

FIG. 3 illustrates that the triblock copolymer membranes and their polymerized counterparts yielded a linear increase of the membrane conductance in time in agreement with previous measurements on pure lipid membranes.

The triblock copolymer membranes gave a mean value of C=0.05 nF (see Table 1). With an area of A=0.02 $mm^2$ and the relative dielectric constant of the PDMS hydrophobic middle block of $\epsilon_1$=2.7 [Sauer, R.O., Mead, D. J., *J. Am. Chem. Soc.*, 1946, 68, 1794], the appropriate calculation yields a hydrophobic thickness of about 10 nm. This value is significantly larger compared to the thickness of a typical lipid membrane (5 nm). Nevertheless, taking into account the size of the triblock copolymer macromolecules, this thickness seems to be reasonable.

For non-polymerized triblock copolymer membranes the breakdown voltage is unusually high, i.e., 1.0±0.2 V, (see Table 1), compared to 0.5 V for conventional black lipid membranes. That means that the energy barrier for pore formation is higher by a factor of 4.

It was expected that the polymerization of the reactive triblock copolymer molecules within these films enforces considerably the mechanical stability of the membranes originally formed via non-covalent interactions and reduces the mobility of the individual triblock copolymer molecules. Indeed, the critical voltage to induce mechanical rupture increased after polymerization to 1.5±0.2 V, i.e. the energy barrier for pore formation is now more than 6 times higher than that of a conventional lipid membrane.

A further parameter revealed by the techniques is the rupture velocity. Assuming the formation of a single pore of circular shape, the analysis of the conductance curves, FIG. 3, yields fast rupture velocities of about 1 $ms^{-1}$ for the non-polymerized membranes. These values are an order of magnitude faster than that observed in lipid membranes. The triblock copolymer films are moreover thicker than conventional low molecular weight lipid membranes.

After the initial defect is formed the pore area starts to increase. Due to the fast relaxation of the membrane potential the contribution of the electrical field is negligible and the kinetics is determined by the material properties of the membrane only. The widening of the pore is driven by the finite surface tension and controlled by the inertia of the film. Interestingly, the velocities of increase of the pore for the polymerized triblock copolymer membranes have been found to be 3 $ms^{-1}$, i.e. a factor of 3 higher than for their non-polymerized counterparts. This may be a result of the crosslinking polymerization that probably has an additional effect on elastic properties of the membrane and on the dynamics of the triblock copolymer molecules. Depending on the length of the hydrophilic PMOXA parts, it has to be expected that the mobility of the triblock copolymer molecules slows down because of their binding to each other.

An additional factor is the delay time between the pulse and the beginning of the membrane rupture. This delay time reflects the ability of the macromolecules to rearrange prior to the start of the pore widening. The delay time of about 50 µs is comparable to those found in lipid membrane. After polymerization the delay time appeared slightly less with 34 µs on average. This would reflect a lower ability of the macromolecules to self-heal a defect as a result to their covalent binding to each other. However, this apparent trend has to be regarded cautiously because of the considerable scattering of the experimental values.

Example 4

Reconstitution Of Channel Proteins In ABA Triblock Copolymer Membranes

For the reconstitution experiments, the well-characterized bacterial porins OmpF and maltoporin were used as model systems [Nikaido, H., *Molecular Microbiology*, 1992, 6, 4, 435; Winterhalter, M., *Colloids and Surfaces A*, 1999, 149, 547; Schiermer, T., Keller, T. A., Wang, Y-F., Rosenbusch, J. P., *Science*, 1995, 267, 512; Eisenberg, B., *Acc. Chem. Res.*, 1998, 31, 117]. Both porins are transmembrane proteins that form trimeric channels in the outer membrane of Gram-negative bacteria. These water-filled channels allow passive diffusion of small solutes like ions, nutrients or antibiotics across the membrane. The incorporation of the protein into a planar freestanding film can directly be monitored using conductivity measurements [Benz, R., Bauer, K., Eur. J. Biochem., 1988, 176, 1; Winterhalter, M., *Colloids and Surfaces A*, 1999, 149, 547].

A first set of experiments was devoted to the question whether such transmembrane proteins can indeed be reconstituted in a preformed PMOXA-PDMS-PMOXA triblock copolymer membrane. For this purpose about 1–5 µL of a porin stock solution (about 0.2–1.5 mg $mL^{-1}$ in 1% octyl-polyoxyethylene, 1 mM $NaN_3$, 100 mM NaCl and 2.5 mM Hepes, pH 7.6) was added on both sides of the chamber. The incorporation of porin into the triblock copolymer membranes was favored by applying a potential of 20 mV across the membrane. The conductance across the freestanding film was measured using Ag/AgCl electrodes and a current amplifier (BLM120, Biologic, Claix, France) (see FIG. 1).

Figure 4:
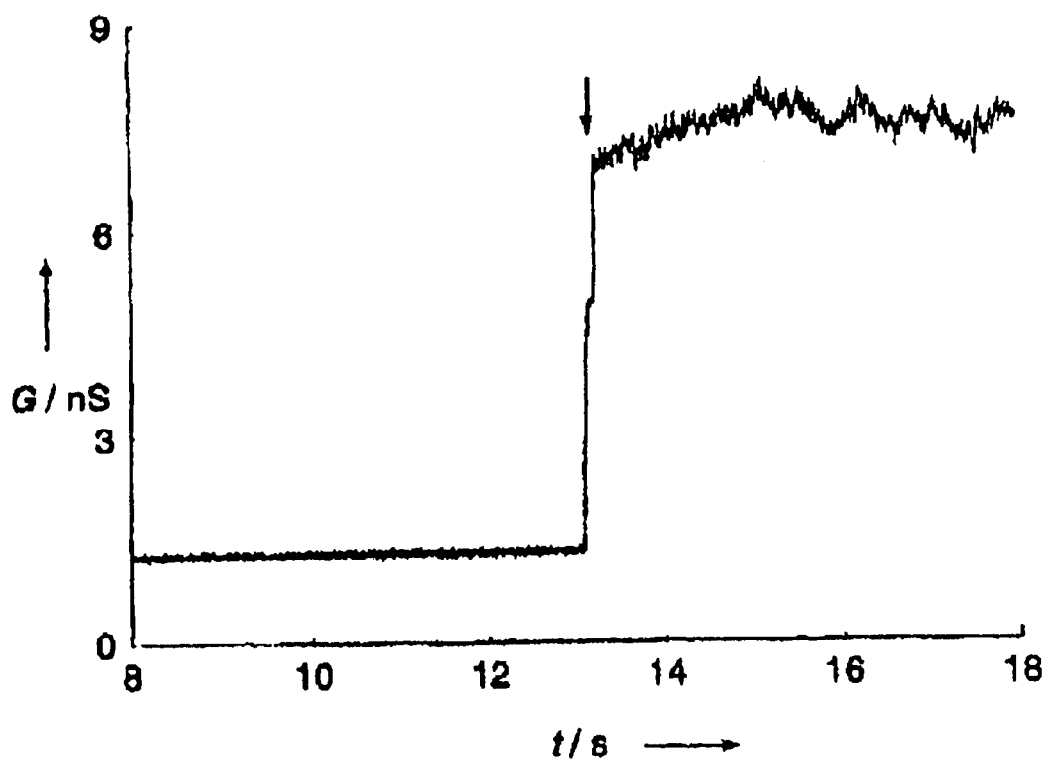
FIG. 4 is a characteristic time course of the conductance across a PMOXA-PDMS-PMOXA triblock copolymer membrane in the presence of the bacterial protein OmpF.

FIG. 4 shows the time course of the conductance across the triblock copolymer membrane in the presence of OmpF.

Surprisingly, despite the extreme thickness of this polymeric membrane, a few minutes after the addition of the porin from the stock solution the conductance increases in a stepwise manner. Each OmpF-trimer contributes a conductance of 2 nS under the given experimental conditions (buffer, temperature) [Benz, R., Schmid, A., Hancock, R. E. W., *J. Bacteriol.*, 1985, 162, 722]. Accordingly, the overall conductance increase of 6 nS corresponds to the insertion of 3 OmpF-trimers into the polymer membrane.

The voltage dependent closure of reconstituted OmpF was tested and no closure up to 200 mV was observed. Similar results were reported for OmpF in conventional solvent containing black lipid films [Muller, D. J., Engel, A., *J Mol. Biol.*, 1999, 285, 1347].

Figure 5:
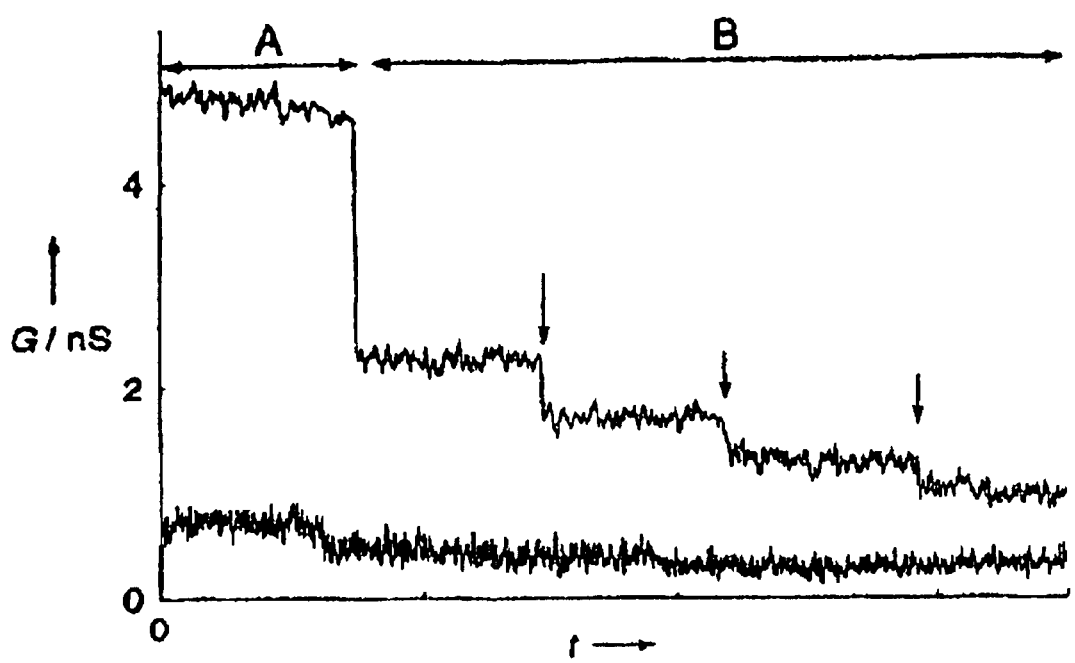
FIG. 5 illustrates the conductance of a maltoporin-containing PMOXA-PDMS-PMOXA triblock copolymer membrane (upper curve) and a protein free membrane (lower curve) during polymerization and the conductance of the maltoporin-containing PMOXA-PDMS-PMOXA triblock copolymer membrane during stepwise addition of 6 $\mu$L of a $10^{-1}$ M maltohexose solution.

In a second series of experiments, a second bacterial porin, LamB protein or maltoporin, was used. Maltoporin forms very narrow channels of about 150 pS at 1 M KCl. Maltoporin possesses stereo-specific binding sites for maltooligosaccharides inside the aqueous channels, which enhances passive diffusion of the sugars [Nikaido, H., *Molecular Microbiology*, 1992, 6, 4, 435; Winterhalter, M., *Colloids and Surfaces A*, 1999, 149, 547; Schiermer, T., Keller, T. A., Wang, Y-F., Rosenbusch, J. P., *Science*, 1995, 267, 512; Wang, Y-F., Dutzler, R., Rizkallah, P. J., Rosenbuch, J. P., Schirmer, T., *J Mol. Biol.*, 1997, 272, 56; Dutzler, R., Wang, Y-F., Rizkallah, P. J., Rosenbuch, J. P., Schirmer, T., *Structure*, 1996, 4, 2, 128]. Using the above described set-up, the incorporation of maltoporin into the polymer membranes was directly monitored. Titration of sugar will drive the sugar into the channel in a concentration dependent manner and cause closure of the channel. From the conductance decrease as a function of sugar concentration the maltooligosaccharide affinity can be obtained [Winterhalter, M., *Colloids and Surfaces A*, 1999, 149, 547]. FIG. 5 shows the time course of the conductance of a maltoporin containing triblock copolymer membrane. For comparison also the conductance of a protein free membrane has been included. Initially the conductance of the maltoporin containing triblock copolymer membrane was about 4 nS higher than that of the protein free membrane. This suggests that 27 maltoporin trimers were inserted.

The same preparation was afterwards polymerized with UV light. Interestingly, the conductance decreased considerably. This could reflect a closure or an expulsion of some of the channel during the crosslinking reaction, probably due to internal stress occurring in the membrane during the polymer chain reaction, which may lead to a steric contraction of the hydrophilic blocks of the polymers. Such a steric contraction should depend sensitively on the length of the hydrophilic blocks. This theory is also supported by the slight conductance decrease observed in the protein-free membrane during the crosslinking reaction. Likely the polymerization induces a reorganization within the films that allows to heal small membrane defects.

The remaining maltoporin-trimers in the polymerized PMOXA-PDMS-PMOXA triblock copolymer membrane were subsequently titrated with maltooligosaccharides. FIG. 5 shows the conductance of the polymerized membrane during stepwise addition of 6 $\mu$L of a $10^{-1}$ M maltohexaose solution. From these data the binding constant between the proteins and the sugar was found to be K=7100 $M^{-1}$. The sugar affinity constants for maltoporin within the polymerized triblock copolymer membrane were the same and in good agreement with previous investigations on maltoporin in conventional lipid membranes [Benz, R., Bauer, K., Eur. *J. Biochem.*, 1988, 176, 1; Winterhalter, M., *Colloids and Surfaces A*, 1999, 149, 547]. Apparently, the conformation of the protein has not been affected by the artificial surrounding within such a polymerized triblock copolymer membrane and its functionality is fully preserved.

Modifications and variations of the present invention will be apparent to those skilled in the art from the forgoing detailed description. All modifications and variations are intended to be encompassed by the following claims. All publications, patents, and patent applications cited herein are hereby incorporated by reference in their entirety.

What is claimed is:

1. A planar membrane formed from amphiphilic copolymers having hydrophobic and hydrophilic segments, wherein the membrane is a bilayer membrane and has a thickness from about 1 nm to 100 nm.

2. The planar membrane of claim 1, wherein the amphiphilic copolymers are ABA copolymers, wherein one of A and B is a hydrophilic polymer and the other is a hydrophobic polymer.

3. The planar membrane of claim 1, wherein the planar membrane is stabilized through crosslinking of the copolymers.

4. The planar membrane of claim 3, wherein the crosslinking comprises end group polymerization.

5. The planar membrane of claim 1, wherein the membrane is a freestanding film.

6. The planar membrane of claim 1 further comprising a molecule incorporated within the membrane.

7. The planar membrane of claim 6, wherein the molecule is a transmembrane protein.

8. The planar membrane of claim 1, wherein the copolymers are biodegradable.

9. The stabilized planar membrane of claim 3, wherein the membrane is biodegradable.

10. A method of making a stabilized planar membrane, comprising; forming a planar membrane from [an] amphiphilic [copolymer] copolymers, wherein the membrane is a bilayer membrane having a thickness from about 1 nm to 100 nm; and stabilizing the planar membrane by crosslinking the copolymers.

11. The method of claim 10, wherein the planar membrane is a freestanding film.

12. The method of claim 10, wherein the copolymers are crosslinked through end group polymerization.

13. The method of claim 10, wherein the amphiphilic copolymer comprises an ABA copolymer, where one of A is hydrophilic and the other is hydrophobic.

14. The method of claim 10, wherein the step of stabilization further comprises crosslinking the copolymers internally.

15. The method of claim 10, further comprising incorporating a molecule into the membrane.

16. The method of claim 15, wherein the molecule is a transmembrane protein.

* * * * *